United States Patent [19]

Vince

[11] Patent Number: 4,742,064
[45] Date of Patent: May 3, 1988

[54] ANTIVIRAL CARBOCYCLIC ANALOGS OF XYLOFURANOSYLPURINES

[75] Inventor: Robert Vince, St. Paul, Minn.

[73] Assignee: Regents of the University of Minnesota, Minneapolis, Minn.

[21] Appl. No.: 774,436

[22] Filed: Sep. 10, 1985

[51] Int. Cl.⁴ .................. C07D 473/32; A61K 31/52
[52] U.S. Cl. ................................. 514/258; 544/276; 544/277; 514/261; 514/262
[58] Field of Search ................ 544/254, 276, 277; 514/258, 262, 261

[56] References Cited

U.S. PATENT DOCUMENTS 4,138,562  2/1979  Vince .................................. 544/326
4,383,114  5/1983  Vince .................................. 544/277
4,543,255  9/1985  Sheally ................................ 544/277

OTHER PUBLICATIONS

H. Lee and R. Vince, J. Pharm. Sci., 69, 1019 (1980).
R. Vince et al., J. Med. Chem. 27, 1358 (1984).
R. Vince et al., J. Med. Chem., 20, 612 (1977).
L. B. Townsend, in Nucleoside Analogues-Chemistry, Biology and Medical Applications, R. T. Walker, E. DeClerq and F. Eckstein, Eds., Plenum Press, NY (1979), at pp. 193–223.

R. Vince et al., Science, 221, 1405 (1983).

*Primary Examiner*—Nicholas S. Rizzo
*Attorney, Agent, or Firm*—Merchant, Gould, Smith, Edell, Welter & Schmidt

[57] ABSTRACT

Biologically-active (6-amino) purine nucleosides of the formula:

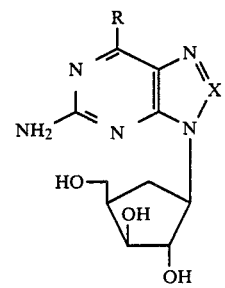

are disclosed wherein X is CH or N, and R is selected from the group consisting of N(Y)(Z), SY, OY and halogen, wherein Y and Z are H, lower(alkyl), phenyl or mixtures thereof; and the pharmaceutically-acceptable salts thereof. The compounds exhibit antiviral and antitumor activity.

12 Claims, 2 Drawing Sheets

ANTIVIRAL CARBOCYCLIC ANALOGS OF XYLOFURANOSYLPURINES

This invention was made with Government support under Grant Number 2R01 CA23263, awarded by the National Institute of Health. The Government has certain rights in this invention.

FIELD OF THE INVENTION

The present invention relates to carbocyclic analogs of purine nucleosides which exhibit antiviral and cytotoxic activity.

BACKGROUND OF THE INVENTION

Despite intensive efforts to discover drugs that may be of value in the systemic treatment of virus infections, such infections have been singularly resistant to chemotherapy. The intracellular and intimate relation to nuclear metabolism of virus reproduction makes it difficult to destroy a virus without irreparable damage to the host cell.

The discovery of the antiviral activity of vidarabine (9-β-D-arabinofuranosyladenine monohydrate) has led to the preparation of a large number of synthetic nucleosides. For example, the synthesis of adenine ("6-amino-purine") nucleoside analogs in which the pentose sugar has been replaced with a hydroxy-substituted cyclopentyl residue has yielded compounds with substantial cytotoxic and antiviral activity. However, the structure-activity relationships between the variously-substituted 9-(cyclopentyl)adenines which have been prepared and tested remain ill-defined.

For example, H. Lee and R. Vince, in *J. Pharm. Sci.*, 69, 1019 (1980) disclosed the 2-amino-6-substituted purines of formula I (R=NH$_2$ or OH, X=CH or N).

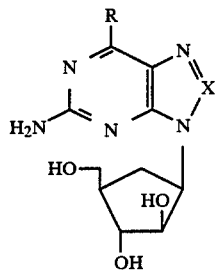

I

In these compounds, the arabinofuranosyl residue has been replaced with a 1α,2β-dihydroxy-5α-hydroxymethylcyclopent-3α-yl moiety where the designations "α" and "β" refer to substituents which are respectively, above and below the plane of the cyclopentane ring as it is depicted in formula I. The compound of formula I where R=NH$_2$ and X=CH exhibited activity against Herpes simplex virus, type 1 (HSV-1), but was inactive against HSV-2. The other compounds of formula I exhibited no significant antiviral activity.

R. Vince et al., in *J. Med. Chem.*, 27, 1358 (1984) disclosed the carbocyclic xylofuronosyl adenine and 8-aza-adenine compounds of formula II (X=CH or N).

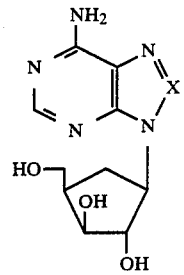

II

The removal of the 2-amino group present in the compounds of formula I (R=NH$_2$) and the inversion of the stereochemistry of the 1,2-dihydroxy substituents on the cyclopentyl ring to yield the compounds of formula II resulted in the loss of antiviral activity. However, compounds of formula II (X=CH) substituted with the cyclopentyl moiety shown in formula I have been disclosed to exhibit substantial activity against HSV-1 and HSV-2. See, R. Vince and S. Daluge, in *J. Med. Chem.*, 20, 612 (1972).

Thus, a substantial need exists for chemotherapeutic agents effective to protect mammalian cells against infection by viruses such as HSV-1, HSV-2, AIDS, varicellazoster, vaccinia, cytomegalovirus and the like.

SUMMARY OF THE INVENTION

The present invention is directed to carbocyclic xylofuranosyl-substituted (2-amino)purines of the formula:

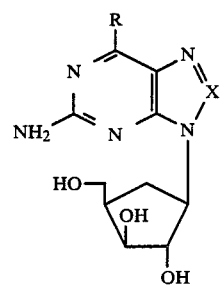

wherein X is CH or N and R is selected from the group consisting of N(Y)(Z), SY, OY and halogen, wherein Y and Z are H, lower(C$_1$-C$_4$)alkyl, phenyl or mixtures thereof, and the pharmaceutically acceptable salts thereof. Preferably R is Cl, OH or NH$_2$. These compounds are effective antiviral and/or cytotoxic agents or are intermediates useful for the preparation thereof. It is believed that the antiviral activity is due to an inhibitory effect on the ability of viruses to infect normal mammalian cells, and to their resistance to in vivo deamination by adenosine deaminase. The present invention is also directed to the intermediate compound of the formula:

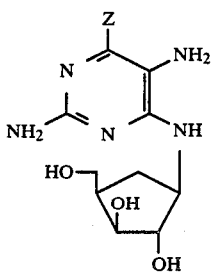

wherein Z is halogen, preferably Cl, which is useful for the preparation of the (2-amino)purines of the invention. Thus, it is expected that the compounds of the present invention will be useful against viral infections or virus-associated tumors.

DETAILED DESCRIPTION OF THE INVENTION

Figure 1:
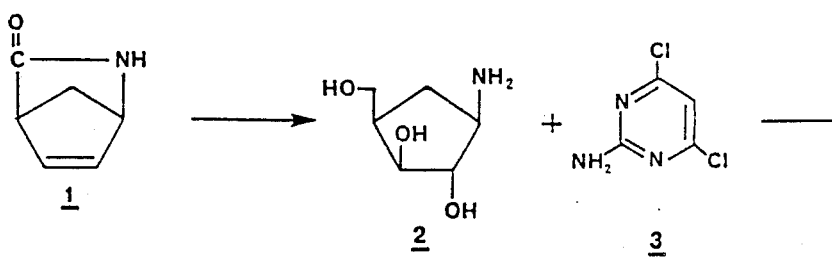
FIGS. 1 and 2 are flow diagrams summarizing the synthesis of the (2-amino)purines of the present invention.
Figure 1:
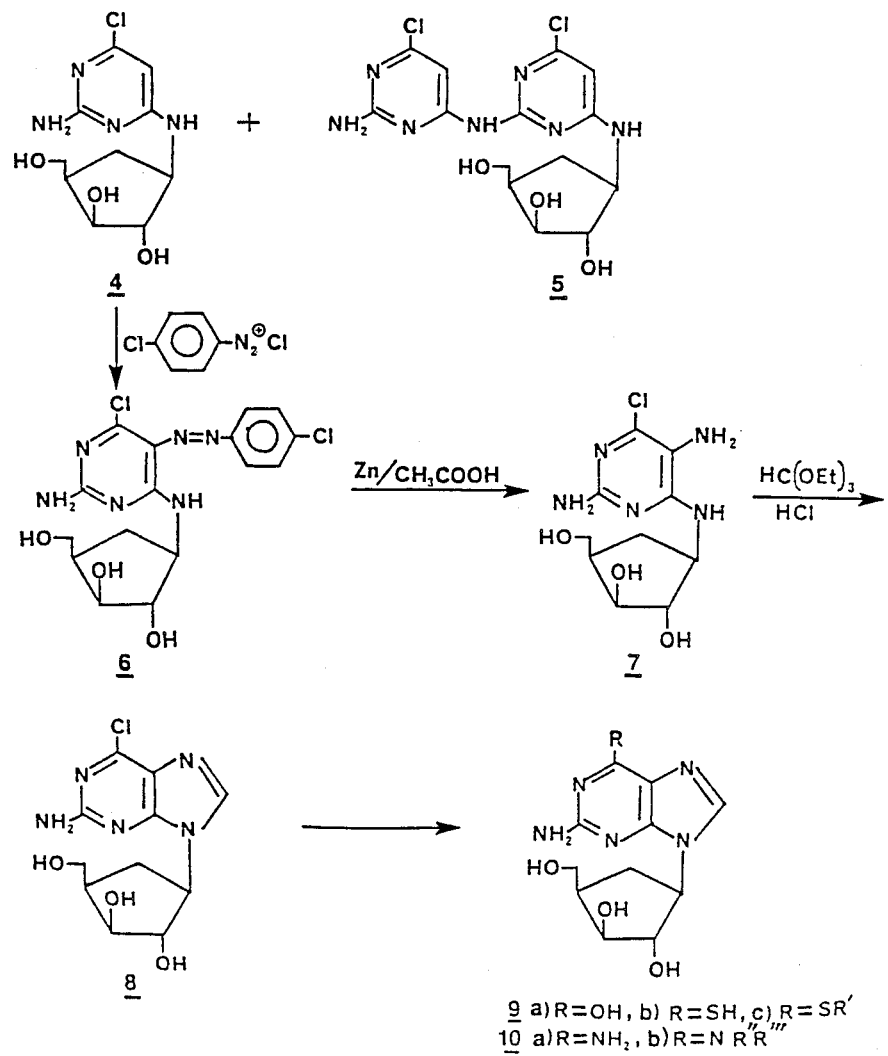

The synthesis of the carbocyclic xylofuranosylaine, (dl)-(1 α,2 β,3 α,5 α)-3-amino-5-(hydroxymethyl)-1,2-cyclopentanediol (2), from the versatile precursor, 2-azabicyclo[2.2.1]hept-5-ene-3-one (1), was accomplished as described by R. Vince et al. in *J. Med. Chem.*, 27, 1358 (1984), the disclosure of which is incorporated by reference herein. As shown in FIG. 1, condensation of 2 with 2-amino-4,6-dichloropyrimidine(3) gave the corresponding pyrimidinylamino derivative (4) along with disubstituted product 5. The assignment of structure 5 is consistent with its infrared, NMR, and spectral analyses. Also, the presence of two NH signals at δ9.82 and δ7.80–7.72 and one NH2 signal at δ6.67 in the NMR spectrum rules out the possibility that both pyrimidine moieties were attacked by the 3-amino group of 2.

The 5-(p-chlorophenylazo) pyrimidine (6) was prepared with p-chlorobenzenediazonium chloride by the method of Shealy and Clayton, in *J. Pharm. Sci.*, 62, 1432 (1973). Reduction of 6 with zinc and acetic acid gave the pyrimidine 7, which was subsequently converted to the 9-substituted 2-amino-6-chloropurine (8) by ring closure with triethyl orthoformate and subsequent mild acid hydrolysis to remove ethoxymethylidenes and formates formed during the reaction.

Treatment of 8 with 1N hydrochloric acid under reflex conditions gave carbocyclic xylofuranosylguanine (9a), while treatment of 8 with liquid ammonia yielded the carbocyclic xylofuranosyl 2,6-diaminopurine (10a).

Treatment of 8 with thiourea in refluxing alcohol, followed by alkaline hydrolysis affords thiol 9b. See L. F. Fieser et al., *Reagents for Organic Synthesis*, John Wiley and Sons, Inc., N.Y. (1967) at pages 1165–1167 and U.S. Pat. No. 4,383,114, the disclosures of which are incorporated by reference herein. Phenyl or alkylthio-derivatives (9c, R′=phenyl or (lower)alkyl) can be prepared from the corresponding thiol 9b by the procedure of U.S. Pat. No. 4,383,114 (Example 6).

Mono- or disubstituted 6-amino compounds of formula 10b (R″=R‴=(lower)alkyl, phenyl or mixtures thereof with H can be prepared by conventional methods for the conversion of halides to secondary or tertiary amines. For example, see I. T. Harrison, et al., *Compendium of Organic Synthetic Methods*, Wiley-Interscience, N.Y. (1971) at pages 250–252. The 6-chloro substituent in compounds 6–8 can be replaced with other halogen atoms by the use of various p-(halo)benzene diazonium chlorides in the conversion of 4 to 6, or by conventional methods of halide-halide exchange.

These conversions are extensively described in the context of purine nucleoside synthesis in *Nucleoside Analogs-Chemistry, Biology and Medical Applications*, R. T. Walker et al., eds., Plenum Press, N.Y. (1979) at pages 193–223, the disclosure of which is incorporated by reference herein.

Figure 2:
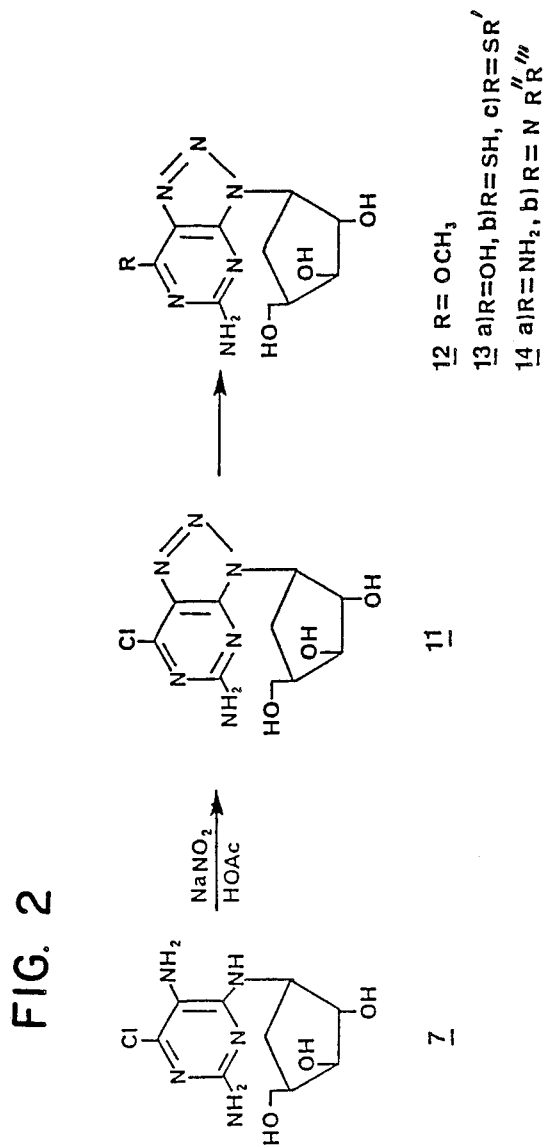

The 8-azapurine analogs were obtained as outlined in FIG. 2. Ring closure 7 with sodium nitrite and acetic acid gave (1 α,2 β,3 α,5 β)-(d1)-3-(5-amino-7-chloro-3H-1,2,3-triazolo[4,5-d]pyrimidin-3-yl)-5-(hydroxymethyl)-1,2-cyclopentanediol (11) in good yield. When 11 was heated in methanol, displacement of chlorine from the heterocyclic ring gave the corresponding methoxy derivative (12) in 80% yield. Acid hydrolysis of 11 gave the 8-aza analog (13a) of the carbocyclic xylofuranosylguanine 9a, whereas treatment of 11 with liquid ammonia gave the 8-aza analog (14a) of the carbocyclic xylofuranosyl-2,6-diaminopurine 10a. Analogs 13b, 13c, and 14b can be prepared as discussed above for analogs 9b, 9c, and 10b, respectively. Pharmaceutically-acceptable acid salts of compounds 8–14 can be prepared as described in U.S. Pat. No. 4,383,114.

The invention will be further described by reference to the following detailed examples, wherein elemental analyses were performed by M-H-W Laboratories, Phoenix, AZ. Melting points were determined on a Mel-Temp apparatus and are corrected. Nuclear Magnetic resonance (NMR) spectra were obtained with a Joel FX 900 FT (89.55-MHZ), infrared spectra with a Perkin-Elmer 237B Spectrometer, and ultraviolet spectra with a Beckman DU-8 recording spectrometer. Thin-layer chromatography (TLC) employed 0.25 mm layers of Merck silica gel 60F-254 and column chromatography used Merck silica gel (230–400 mesh). Mass spectra (MS) were obtained with an AEI Scientific Apparatus Limited MS-30 mass spectrometer. Low-resolution mass spectra were obtained for all compounds and the molecular ion and fragmentation patterns were reasonable for the assigned structures. Temperatures are given in °C. unless otherwise noted.

EXAMPLE 1

(d1)-(1 α,2 β,3 α,5 α)-3-[(2-Amino-6-chloro-4-pyrimidinyl)amino]-5-(hydroxymethyl)-1,2-cyclopentanediol(4). To 7.65 g (52.05 mmol) of (d1)-(1 α,2 β,3 α,5 α)-3-amino-5-(hydroxymethyl)-1,2-cyclopentanediol (2) in 200 ml 1-butanol and 25 ml methanol was added a mixture of 9.39 g (57.24 mmol) 2-amino-4,6-dichloropyrimidine, 30 ml triethylamine and 50 ml 1-butanol. The resulting solution was refluxed for two days. The solvent was evaporated in vacuo and the residue was partitioned between water and dichloromethane. The insoluble disubstituted product (5) was removed by filtration to afford 5.90 g (39%) of an off-white solid. The aqueous solution was washed with dichloromethane (3×30 ml) to remove unreacted 2-amino-4,6-dichloropyrimidine and evaporated to dryness. The residue was then evaporated onto coarse silica gel (70–230 mesh) which was subsequently applied to the top of a flash chromatography (230–400 mesh silica gel) column. The column was eluted with acetone. Product fractions (Rf=0.31) were combined. The solvent was removed in vacuo to yield 4 as an off-white solid (4.84 g). An analytical sample was recrystallized twice from methanol/methylene chloride, mp 199°-200°; UV: εmax (λx 10$^{-3}$) 271.4 (12.6), 240.6 (15.2) in 0.1 N HCl, 286.4 (10.1), 238.1 (11.1), 211.4 (26.3) in H$_2$O, and 286.4 (10.1), 238.9 (11.0), 216.4 (16.6) in 0.1N NaOH; MS (70ev, 200°): m/e 274 (M$^+$), 256 (M$^+$-H$_2$O), 243 (M$^+$-CH$_2$OH), 225 (M$^+$-CH$_2$OH-H$_2$O), 171 (B+28), 145 (B+2H), 144 (B+H), 143 (B), 128, 98, 67, 43; IR (KBr): 3500-3200 cm$^{-1}$ (NH, OH), 1660 and 1595 (C=C, C=N); NMR (90 MHz, dimethylsulfoxide-d$_6$): δ 7.12 (br s, 1H, NH), 6.40 (s, 2H, NH$_2$), 5.80 (s, 1H, Ar-H), 4.85-4.68 (2d, 2H, 2CHOH), 4.55-4.20 (t, 1H, CH$_2$OH), 3.62-3.12 (m, 5H, 2C$\overline{H}$OH, CH$_2$OH, CHN), 2.08-1.19 (m, 3H, CHCH$_2$O$\overline{H}$, C$\overline{H}_2$); Anal. (C$_{10}$H$_{15}$N$_4$O$_3$Cl·½H$_2$O) C, H, $\overline{N}$, Cl.

An analytical sample of 5 was prepared by recrystallization from ethanol, mp 275°-276°; MS (20 ev, 200°): m/e 401 (M$^+$), 370 (M$^+$-CH$_2$OH), 342 (M$^+$-59), 298 (B+28), 272 (B+2H), 271 (B+H), 270 (B); IR (KBr): 3500-3200 cm$^{-1}$ (NH, OH), 1595, 1450, 1210, 980, 910, 815; NMR (90 MHz, dimethylsulfoxide-d$_6$): δ 9.82 (s, 1H, NH), 7.80-7.72 (br d, 1H, NH), 7.54 and 6.16 (2s, 2H, 2Ar-H), 6.67 (s, 2H, NH$_2$), 5.05-4.69 (2d, 2H, 2CHOH), 4.33-4.23 (t, 1H, CH$_2$O$\overline{H}$), 3.94-3.09 (m, 5H, 2CHO$\overline{H}$, CH$_2$OH, CHN), 2.15-1.33 (m, 3H, CHCH$_2$OH, $\overline{C}$H$_2$); Anal. (C$_{14}$H$_{17}$N$_7$O$_3$Cl$_2$·H$_2$O) C, H, $\overline{N}$, Cl.

EXAMPLE 2

(dl)-(1 α, 2 β, 3 α, 5 α)-3-[[2-Amino-6-chloro-5[(4-chlorophenyl)-azo]-4-pyridiminyl]amino]-5-(hydroxymethyl)-1,2-cyclopentanediol (6). A cold (0°-5°) solution of p-chlorobenzenediazonium chloride was prepared by adding a solution of 650 mg (9.50 mmol) sodium nitrite in 5 ml water to a solution of 1.15 g (9 mmol) p-chloroaniline dissolved in 5 ml of 12N HCl and 15 ml water and cooled in an ice-salt bath. The cold solution of p-chlorobenzenediazonium chloride was added to a mixture of 2.15 g (7.8 mmol) of 4, 17 g sodium acetate trihydrate, 40 ml acetic acid and 40 ml water at 25° C. The mixture as stirred for eighteen hours at 25° C., then cooled in an ice bath. A yellow crystalline precipitate (6) was collected by filtration, washed with cold water, and dried: yield, 2.22 g (69%).

The product was recrystallized from methanol to yield 6 as a yellow powder, mp 233°-236°; UV λ max in nm (εX10$^{-3}$) 372.2 (32.4), 280.6 (11.3), 240.6 (24.6), 204.7 (21.9) in 0.1N HCl, 389.8 (41.6), 315.6 (9.5), 280.6 (15.9), 219.8 (23.9) in MeOH, and 384.75 (16.3), 215.6 (17.2) in 0.1N NaOH; MS (70 ev, 200): m/e 412 (M$^+$), 286, 283 (B+2H), 281 (B), 268, 238, 210, 182, 158, 146, 127, 114, 95, 65, 43; IR (KBr): 3400-3100 (OH, NH), 1655, 1645, 1590, 1570 cm$^{-1}$ (Ar, C=C, C=N, NH); NMR (90 MHz, dimethylsulfoxide-d$_6$) δ 7.78-7.54 (m, 7H, Ar-H, NH$_2$, NH), 5.06-5.02 (m, 2H, 2CHOH), 4.41-4.30 (t, 1H, CH$_2$OH), 3.89-3.30 (m, 5H, CH$_2$O$\overline{H}$, 2CHOH, CHN) 2.31-1.$\overline{22}$ (m, 3H, CHCH$_2$OH, $\overline{C}$H$_2$); Anal. (C$_{16}$$\overline{H}$$_{18}$N$_6$O$_3$Cl$_2$·H$_2$O) C, H, $\overline{N}$, Cl.

EXAMPLE 3

(dl)-(1 α, 2 β, 3 α, 5 α)-[(2,5-Diamino-6-chloro-4-pyridiminyl)amino]-5-(hydroxymethyl)-1,2-cyclopentanediol (7). A solution of 2.00 g (4.84 mmol) of 6, 3.2 g zinc dust (200 mesh), 1.6 ml acetic acid, 75 ml water and 75 ml ethanol was refluxed under an atmosphere of nitrogen. The reaction was followed by TLC and was completed within 1.5 hours. Excess zinc was removed by filtration, and the solvent was evaporated to dryness. The brown residue was dissolved in 50 ml water, and the aqueous solution was washed with methylene chloride to remove p-chloroaniline. After removal of water under reduced pressure, the residue was evaporated onto coarse silica gel, (70–230 mesh) and applied to the top of a flash chromatography column (230–400 mesh silica gel). The column was eluted with methylene chloride-methanol (4:1). The product fractions (Rf=0.28) were collected, combined, and evaporated to dryness and gave 759 mg (54%) of a pink solid.

Recrystallization from methanol-methylene chloride, and then from water afforded 7 as a light pink solid, mp 187°-190°; UV: λmax (εX10$^{-3}$) 295.6 (8.3), 238.9 (16.3), 210.6 (16.2) in 0.1N HCl, 303.1 (8.8), 204.8 (18.9) in H$_2$O; and 303.1 (8.9), 224.8 (12.2) in 0.1N NaOH; MS (70 ev, 200°): m/e 289 (M$^+$), 240 (B+14), 160 (B+2H), 15 g (B+H), 158 (B); IR (KBr): 3500-3100 cm$^{-1}$ (NH, OH), 1635, 1605, 1510 (C=C, C=N, NH); NMR (90 MHz, dimethylsulfoxide-d$_6$): δ 6.46-6.38 (d, 1H, NH), 5.66 and 3.93 (2d, 4H, 2NH$_2$), 4.82-4.69 (2d, 2H, 2CHOH), 4.31-4.19 (t, 1H, CH$_2$OH), 3.72-3.32 (m, 5H, 2CHO$\overline{H}$, CH$_2$OH, CHN), 2.17-1.35 (m, 3H, CHCH$_2$OH, $\overline{C}$H$_2$); Anal. (C$_{10}$H$_{16}$N$_5$O$_3$Cl) C, H, N, Cl.

EXAMPLE 4

(dl)-(1 α, 2 β, 3 α, 5 α)-3-(2-Amino-6-chloro-9H-purin-9-yl)-5-(hydroxymethyl)-1,2-cyclopentanediol (8). A solution of 100 mg (0.345 mmol) of 7 and 3 ml dry dimethylformamide was cooled to 0° and 5 ml of freshly distilled triethylorthoformate and 0.1 ml of concentrated HCl were added. The resulting mixture was stirred under nitrogen at 25° C. for 24 hours. The solvent was evaporated in vacuo to a dark red syrup. The syrup was dissolved in 10 ml of 50% acetic acid and stirred at 25° C. for 4 hours. The solvent was then removed under reduced pressure and the residue was stirred with methanolic ammonia (10% NH$_3$) at 25° C. for 4 hours. The volatile materials were removed in vacuo and the product was dissolved in methanol-methylene chloride and refrigerated overnight. The crystallized product was removed by filtration to yield 52.9 mg (52%) of 8 as a light pink solid.

An analytical sample was recrystallized from water to give 8 as an off-white solid, mp 165°-167°; UV: λmax (εX10$^{-3}$) 313.1 (7.5), 243.1 (6.2), 221.4 (25.6) in 0.1N HCl, 306.4 (7.4), 223.9 (25.9) in H$_2$O; and 307.2 (7.8), 249.8 (7.1), 223.9 (24.6) in 0.1N NaOH; MS (20 ev, 200°): m/e 299 (M$^+$), 282 (M$^+$-OH), 268 (M$^+$-CH$_2$OH), 250 (M$^+$-CH$_2$OH-H$_2$O), 196 (B+28), 170 (B+2), 169 (B+1), 168 (B), 134, 81; IR (KBr): 3500-3000 cm$^{-1}$ (NH$_2$, OH), 1635, 1560, 1465 (C=C, C=N); NMR (90 MHz dimethylsulfoxide-d$_6$): δ8.15 (s, 1H, Ar-H), 6.86 (s, 2H, NH$_2$), 5.36-5.05 (2d, 2H, 2CHOH), 4.53-4.38 (t, 1H, CH$_2$OH), 4.17-3.11 (m, 5H, 2CHO$\overline{H}$, CH$_2$OH, CHN), 2.26-1.70 (m, 3H, CHCH$_2$OH, $\overline{C}$H$_2$); Anal. (C$_{11}$H$_{14}$N$_5$O$_3$Cl) C, H, N, Cl.

EXAMPLE 5

(dl)-2-Amino-1,9-dihydro-9-[(1 α,2 β,3 α,4 α)-2,3-dihydroxy-4-(hydroxymethyl)cyclopentyl]-6H-purin-6-one (9a). A solution of 100 mg (0.345 mmol) of 7 and 3 ml dry dimethylformamide was cooled to 0° C. and 5 ml of freshly distilled triethylorthoformate and 0.1 ml conc. HCl were added. The reaction mixture was stirred under nitrogen at room temperature for 24 hours. The solvent was evaporated and the residue was dissolved in 10 ml of 1N HCl. The solution was refluxed for 5 hours and then the water was evaporated and azeotroped with absolute ethanol. The liquid residue was dissolved in a small amount of water and the solution was neutralized to pH 6 with 1N NaOH. A white precipitate formed immediately and the suspension was refrigerated. The solid product was collected by filtration and washed with cold water to yield 63.2 mg of 9a (65%) as an off-white powder, mp 254°–256°.

An analytical sample was recrystallized from water, mp 291°–293°; UV: λmax ($\epsilon \times 10^{-3}$) 255.6 (12.4), 202.2 (41.75) in 0.1N HCl, 253.1 (14.7), 189.8 (31.7) in $H_2O$, and 268.1 (12.4), 217.2 (18.9) in 0.1N NaOH; MS (70 ev, 200°): m/e 281 (M+), 264 (M+-OH), 178 (B+28), 152 (B+2H), 128, 98, 81, 67, 43; IR (KBr): 3400–3150 cm$^{-1}$ (NH, OH), 1725 (C=O), 1640, 1550, 1490 (C=C, C=N, NH); NMR (90 MHz, dimethylsulfoxide-$d_6$): δ 10.54 (s, 1H, NH), 7.71 (s, 1H, Ar-H), 6.39 (s, 2H, $NH_2$), 5.32–5.04 (2d, 2H, 2CHOH), 4.41–4.30 (t, 1H, $CH_2OH$), 4.24–3.32 (m, 5H, 2CHOH, $CH_2OH$, CHN), 2.28–1.38 (m, 3H, $CHCH_2OH$, $CH_2$); Anal. ($C_{11}H_{15}N_5O_4 \cdot 1\frac{1}{2}H_2O$) C, H, N.

EXAMPLE 6

(dl)-1 α,2 β,3 α,5 α)-3-(2,6-Diamino-9H-purin-9-yl)-5-(hydroxymethyl)-1,2-cyclopentanediol (10a). A solution of 61.2 mg (0.204 mmol) of the chloro compound, 8, in 2 ml methanol was transferred into a stainless steel bomb and the methanol was evaporated by a stream of nitrogen. Excess ammonia was added and the sealed bomb was heated at 80° for 2 days. Evaporation of the ammonia left a yellow residue which was dissolved in 5 ml of hot water. Refrigeration of the solution yielded 41.0 mg (72%) of pale yellow semisolid. Recrystallization from water afforded 10a as a pale yellow powder, mp 234°–237°; UV: λ max ($\epsilon \times 10^{-3}$) 291.4 (9.7), 253.1 (9.5), 218.9 (20.8) in 0.1N HCl; 279.8 (10.5), 255.6 (8.6), 215.6 (28.1) in $H_2O$; and 280.6 (10.2), 255.6 (8.1), 218.9 (22.5) in 0.1N NaOH; MS (70 ev, 200°): m/e 280 (M+), 263 (M+-OH), 249 (M+-$CH_2OH$), 231 (M+-$CH_2OH$-$H_2O$), 177 (B+28), 163 (B+14), 151 (B+2), 150 (B+1), 149 (B), 134, 108, 57, 43, 28; IR (KBr): 3600–3100 cm$^{-1}$ (OH, $NH_2$), 1665, 1600, 1495 (C=C, C=N, NH); NMR (90 MHz, dimethylsulfoxide-$d_6$): δ 7.73 (s, 1H, Ar-H), 6.69 (s, 2H, $NH_2$), 6.61 (s, 2H, $NH_2$), 5.86–5.77 (m, 2H, 2CHOH), 4.36–3.67 (m, 6H, CHN, $CH_2OH$, 2CHOH, $CH_2OH$), 2.21–1.82 (m, 3H, $CHCH_2OH$, $CH_2$); Anal. ($C_{11}H_{16}N_6O_3$) C, H, N.

EXAMPLE 7

(dl)-(1 α,2 β,3 α,5 α)-3-(5-Amino-7-Chloro-3H-1,2,3-triazalo [4,5-d]pyrimidin-3-yl)-5-(hydroxymethyl)-1,2-cyclopentanediol (11). A solution of 26.0 mg (0.380 mmol) of sodium nitrite in 1 ml water was drop-wise added to a 0° C. solution of 100 mg (0.345 mmol) of 7 in 1 ml water and 0.5 ml of glacial acetic acid. The solution was stirred at 0° for 2 hours and at 25° C. for 1 hour. The solvent was removed in vacuo (below 20°) and the residue was evaporated onto silica gel and then applied to the top of a flash chromatography column. The column was eluted with methylene chloride-methanol (4:1). The product fractions were collected (Rf=0.53), combined, and concentrated in vacuo to obtain 73.0 mg (70%) colorless solid, mp softens at 130°–150° and melts at 220°–230°.

An analytical sample of 11 was obtained by recrystallization from methanol, mp softens at 121° and melts at 220°–223°; UV: λmax ($\epsilon \times 10^{-3}$) 314.8 (8.6), 225.6 (24.1) in 0.1N HCl; 314.8 (8.2), 225.6 (24.4) in $H_2O$, and 222.2 (24.3) in 0.1N NaOH; MS (20 ev, 250°): m/e 283 (M+-OH), 171 (B+2H), 170 (B+H), 169 (B), 144, 112, 84, 69; IR (KBr): 3600–3250 cm$^{-1}$ (OH, $NH_2$), 1650, 1610, 1470 (C=C, C=N, NH); NMR (90 MHz, dimethylsulfoxide-$d_6$): δ 7.60 (s, 2H, $NH_2$), 5.35–5.29 (d, 1H, CHOH), 5.00–4.95 (d, 1H, CHOH), 4.62–3.60 (m, 6H, CHN, $CH_2OH$, $CH_2OH$, 2CHOH), 2.23–2.15 (m, 3H, $CHCH_2OH$, $CH_2$); Anal. ($C_{10}H_{13}N_6O_3Cl \cdot H_2O$) C, H, N, Cl.

EXAMPLE 8

(dl)-(1 α,2 β,3 α,5 α)-3-(5-Amino-7-methoxy-3H-1,2,3-triazalo [4,5-d]pyrimidin-3-yl)-5-(hydroxymethyl)-1,2-cyclopentanediol (12). A solution of 54.1 mg (0.179 mmol) of 11 in methanol was refluxed for 1 hour. The solvent was evaporated to dryness to obtain 42 mg (80%) of 12 as a colorless semisolid. Crystallization from methanol gave 28.2 mg of 12 (53%) as a pure solid product, mp 157°–159°; UV: λmax ($\epsilon \times 10^{-3}$) 282.2 (10.7), 213.9 (23.6) in 0.1N HCl, 287.2 (9.7), 216.4 (23.4) in $H_2O$; and 285.6 (10.6), 218.9 (22.9) in 0.1N NaOH; MS (30 ev, 220°): 296 (M+), 283, 247 (M+-$CH_2OH$-$H_2O$), 223, 209, 181, 167 (B+2H), 166 (B+H), 165 (B), 139, 110, 96, 83, 67, 53, 43; IR (KBr): 3500–3200 cm$^{-1}$ ($NH_2$, OH) 1665, 1610, 1465 (C=C, C=N, NH); NMR (90 MHz, dimethylsulfoxide-$d_6$): δ 7.07 (s, 2H, $NH_2$), 5.34–5.28 (d, 1H, CHOH), 4.99–4.93 (d, 1H, CHOH), 4.58–3.51 (m, 6H, CHN, $CH_2OH$, $CH_2OH$, 2CHOH), 4.05 (s, 3H, $OCH_3$), 2.47–1.55 (m, 3H, $CHCH_2OH$, $CH_2$); Anal. ($C_{10}H_{13}N_6O_3Cl \cdot H_2O$) C, H, N.

A similar procedure can be employed to replace the chloro substituent of 8 with (lower)alkoxy substituents.

EXAMPLE 9

(dl)-5-Amino-3,6-dihydro-3-[(1 α,2 β,3 α,5 α)-2,3-dihydroxy-4-(hydroxymethyl)cyclopentyl]-7H-1,2,3-triazalo[4,5-d]pyrimidin-7-one (13a). A solution of 91.3 mg (0.304 mmol) of 11 in 10 ml 1N HCl was refluxed for 5 hours. The solvent was removed in vacuo and the resulting yellow solid was crystallized from water and afforded 47.0 mg (55%) of pale yellow powder; mp 235°–238° dec.

A second recrystallization from water gave pure 13a as pale yellow crystalline solid, mp 241°–244° dec.; UV: λ max ($\epsilon \times 10^{-3}$) 253.9 (12.3), 207.2 (20.8) in 0.1N HCl, 253.1 (12.4), 203.1 (23.1) in $H_2O$; and 278.9 (11.6), 220.6 (25.6) in 0.1N NaOH; MS (20 ev, 200°): m/e 187, 167, 153 (B+2H), 134, 121, 107, 84, 70; IR (KBr): 3600–3200 cm$^{-1}$ ($NH_2$, OH), 1710 (C=O), 1600, 1530 (C=C, C=N), NMR (90 MHz dimethylsulfoxide-$d_6$): δ 11.20 (s, 1H, NH), 7.18 (s, 2H, $NH_2$), 5.37–5.63 (d, 1H, CHOH), 5.02–4.96 (d, 1H, CHOH), 4.41–3.32 (m, 6H, CHN, $CH_2OH$, $CH_2OH$, 2CHOH), 2.28–2.01 (m, 3H, $CHCH_2OH$, $CH_2$); Anal. ($C_{10}H_{14}N_6O_4 \cdot \frac{3}{4}H_2O$) C, H, N.

EXAMPLE 10

(dl)-(1 α,2 β,3 α,5 α)-3-(5,7-Diamino-3H-1,2,3-triazalo[4,5-d]pyrimidin-3-yl)-5-(hydroxymethyl)-1,2-cyclopentanediol (14a). A mixture of 94.1 mg (0.313 mmol) of 11 in liquid ammonia was heated in a stainless steel bomb at 80° for 48 hours. Evaporation of ammonia left a solid residue which was crystallized from water and afforded 47.2 mg (54%) pale yellow solid, mp 219°–224°. Recrystallization from water afforded pure 14a as a pale yellow powder, mp 231°–233°; UV: −λmax ($\epsilon \times 10^{-3}$) 286.4 (8.1), 256.4 (10.1), 213.9 (26.6)

in 0.1N HCl; 287.2 (11.3), 260.6 (6.4), 223.9 (27.2) in H$_2$O; and 286.4 (11.6), 260.6 (6.8), 223.9 (28.5) in 0.1N NaOH; MS (30 ev, 330°): m/e 281 (M+), 232, 194, 163, 152 (B+2H), 150 (B), 126, 113, 110, 43; IR (KBr): 3600–3250 cm$^{-1}$ (OH, NH$_2$), 1610, 1645, 1460 (C=C, C=N, NH); NMR (90 Mhz, dimethylsulfoxide-d$_6$): δ7.53 (s, 2H, NH$_2$), 6.34 (s, 2H, NH$_2$), 5.37–5.31 (d, 1H, CHOH), 5.06–5.00 (d, 1H, CHOH), 4.55–3.52 (m, 6H, C$\underline{\text{H}}$N, C$\underline{\text{H}}_2$OH), CH$_2$OH, 2CHO$\underline{\text{H}}$), 2.26–2.05 (m, 3H, C$\underline{\text{H}}$CH$_2$OH, $\overline{\text{C}}$H$_2$); Anal. (C$_{10}\overline{\text{H}}_{15}$N$_7$O$_3$.¼H$_2$O) C, H, N.

EXAMPLE 11

(d1)-(1 α,2 β,3 α,5 α)-3-(2-Amino-6-mercapto-9H-purin-9-yl)-5-(hydroxymethyl)-1,2-cyclopentanediol (9b). A solution of 1.09 mmol of 8 and 1.86 mmol of thiourea in 1-propanol (8 ml) is refluxed for 0.75 hour. The reaction mixture is cooled and the precipitate isolated by filtration and washed with 1-propanol. The isothiourea hydrochloride powder is refluxed for 2 hours with aqueous sodium hydroxide according to the procedure of G. G. Urquhart et al., *Org. Syn. Coll. Vol.*, 3, 363 (1955) to yield 9b. A similar procedure is used to prepare 13b from 11.

EXAMPLE 12

(1 α,2 β,3 α,5 α)-d1-3-(2-Amino-6-methylthio-9H-purin-9-yl)-5-hydroxymethyl)-1,2-cyclopentanediol (9c, R'=CH$_3$). A mixture of crude 9b (0.62 mmol), methyl iodide (0.25 ml), 1.0N NaOH (0.62 ml) and 2.0 ml water is stirred at 25° C. for 4 hours. The resulting solution is evaporated to dryness and the residue chromatographed on a column of silica gel G (Brinkman, 20 g, packed in CHCl$_3$). Elution with methanol-CHCl$_3$ affords 9c, R'=CH$_3$.

Cytotoxicity Assay

The ED$_{50}$ cytotoxicity concentrations determined for analogs 8, 9a, 10a, 11, 12, 13a and 14a in the P-388 mouse leukemia cell culture assay are given in Table I. Carbocyclic nucleosides 9a, 13a, and 14a exhibited significant cytotoxicities in this assay. The 8-aza guanine and purine analogs 13a and 14a are more active than the corresponding guanine and purine analogs, 9a and 10a.

TABLE I

Inhibitory Concentrations of Carbocyclic Xylofuranosides of 2-Amino-6-substituted-purines and 2-Amino-6-substituted-8-azapurines for P-388 Leukemia Cells in Cultures.*

| Compound | ED$_{50}$, μM |
|---|---|
| 8 | 220.0 |
| 9a | 8.9 |
| 10a | 39.0 |
| 11 | 50.0 |
| 12 | 63.0 |
| 13a | 1.6 |
| 14a | 5.3 |

*Assay Technique: R. G. Almquist and R. Vince, J. Med. Chem., 16, 1396 (1973).

Antiviral Assay

Analogs 9a, 10a, 13a, and 14a were evaluated for in vitro antiviral activity against HSV-1. Analogs 9a and 13a were further evaluated for activity against HSV-2. The analogs were evaluated by a cytopathogenic effects (CPE)-inhibition procedure. The host cell culture systems employed were pre-grown Vero cell monolayers. The results of these assays are summarized in Table II, below. A virus rating of one or greater is indicative of a compound with a favorable balance between its antiviral effect and its cytotoxicity to the host cells.

TABLE II

| Compound No. | HSV-1 (E-377) VR* | HSV-1 (E-377) MIC$_{50}$** | HSV-2 (MS) VR* | HSV-2 (MS) MIC$_{50}$* |
|---|---|---|---|---|
| 9a | 5.6 | 3.0 | 3.9 | 23.5 |
| 10a | 2.7 | 85.0 | — | — |
| 13a | 2.4 | 60.8 | 1.3 | 92.2 |
| 14a | 2.0 | 66.9 | — | — |
| Positive Control: Ara-A | 1.7 | 21.8 | 1.6 | 40.6 |

*VR = virus rating: A measurement of selective antiviral activity which takes into account the degree of inhibition of virus-induced cytopathogenic effects (CPE) and the degree of cytotoxicity produced by the test compound, determined by a modification of the method of Ehrlich et al. (Ann. N.Y. Acad. Sci. 130: 5–16, 1965). A VR ≧ 1.0 indicates definite (+) antiviral activity, a VR of 0.5–0.9 indicates marginal to moderate (+) antiviral activity, and a VR < 0.5 usually indicates no (—) significant antiviral activity.
**MIC$_{50}$ = Minimum inhibitory concentration required for 50% inhibition of virus-induced CPE (in μg/ml).

The data presented in Table II demonstrate that analogs 9a, 10a, 13a and 14a exhibit substantial antiviral activity against HSV-1, while 9a and 13a are also active against HSV-2 ("genital herpes"). However, while the 2-amino-8-aza-guanine analog 13a exhibited inhibition at the lowest concentration in the cytotoxicity assay, 2-aminoguanine analog 9a exhibited the best profile of activity in the antiviral assay. Of the analogs listed in Table II, only 13a exhibited any significant activity against an influenza virus.

The invention comprises the biologically-active xylofuranosyl purines as disclosed or the pharmaceutically acceptable salts or esters thereof, together with a pharmaceutically acceptable carrier for administration in effective non-toxic dose form. Pharmaceutically acceptable salts may be salts of organic acids, such as acetic, lactic, malic, or p-toluene sulphonic acid, and the like as well as salts of pharmaceutically acceptable mineral acids, such as hydrochloric or sulfuric acid, and the like. Other salts may be prepared and then converted by conventional double decomposition methods into pharmaceutically acceptable salts directly suitable for purposes of treatment of viral infections in mammals or for the prevention of viral contamination of physiological fluids such as blood or semen in vitro.

Pharmaceutically acceptable carriers are materials useful for the purpose of administering the present analogs and may be solid, liquid or gaseous materials, which are otherwise inert and medically acceptable and are compatible with the active ingredients. Thus, the present active compounds can be combined with the carrier and added to physiological fluids in vitro or administered in vivo parenterally, orally, used as a suppository or pessary, applied topically as an ointment, cream, aerosol, powder, or given as eye or nose drops, etc., depending upon whether the preparation is used for treatment of internal or external viral infections.

For internal virus infections, the compositions may be administered orally or parenterally at effective non-toxic antivirus dose levels of about 50 to 750 mg/kg/day of body weight given in one dose or several smaller doses throughout the day. For oral administration, fine powders or granules may contain diluting, dispersing and/or surface active agents and may be presented in water or in a syrup; in capsules in the dry state, or in a non-aqueous solution or suspension; in tablets, or the like. Where desirable or necessary, flavoring, preserving, suspending, thickening or emulsifying agents may be included. For parenteral administration or for administration as drops, as for eye infections, the compounds may be presented in aqueous solution in an effective nontoxic dose in concentration of from about 0.1 to 10 percent w/v. The solutions may contain antoxidants, buffers, and the like. Alternatively, for infections of the eye or other external tissues, the compositions are preferably applied as a topical ointment or cream in concentration of about 0.1 to 10 percent w/v.

It is apparent that many modifications and variations of this invention may be made without departing from the spirit and scope thereof. The specific embodiments described are given by way of example only and the invention is limited only by the terms of the appended claims.

What is claimed is:

1. A method for protecting mammalian cell against infection by a virus comprising bringing said cells into contact with an effective amount of the compound in a pharmaceutically-acceptable carrier.

2. The method of claim 1 wherein said virus is HSV-1 or HSV-2.

3. A compound of the formula:

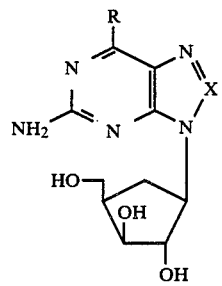

wherein X is CH and R is selected from the group consisting of N(Y)(Z), SY, OY and halogen, wherein Y and Z are H, lower(alkyl) or phenyl; and the pharmaceutically-acceptable salts thereof.

4. The compound of claim 3 wherein R is chloro.
5. The compound of claim 3 wherein R is $NH_2$ or OH.
6. The compound of claim 5 wherein R is $NH_2$.
7. The compound of claim 5 wherein R is OH.
8. A compound of the formula:

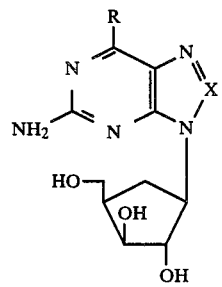

wherein X is N and R is selected from the group consisting of N(Y)(Z), SY, OY and halogen, wherein Y and Z are H, lower(alkyl), phenyl or mixtures thereof; and the pharmaceutically-acceptable salts thereof.

9. The compound of claim 8 wherein R is chloro.
10. The compound of claim 8 wherein R is $NH_2$ or OH.
11. The compound of claim 10 wherein R is $NH_2$.
12. The compound of claim 10 wherein R is OH.

* * * * *

UNITED STATES PATENT AND TRADEMARK OFFICE
CERTIFICATE OF CORRECTION

PATENT NO. : 4,742,064

DATED : May 3, 1988

INVENTOR(S) : Robert Vince

It is certified that error appears in the above-identified patent and that said Letters Patent is hereby corrected as shown below:

At column 3, line 26, for "carbocvclic" read --carbocyclic--.

At column 3, line 26, for "xylofuranosylaine" read --xylofuranosylamine--.

At column 3, line 32, for "bv" read --by--.

At column 5, line 6, for "$\varepsilon max\ (\lambda x\ 10^{-3})$" read --$\lambda\ max\ (\varepsilon\ x\ 10^{-3})$--.

At column 11, line 32, for "mammalian cell" read --mammalian cells--.

At column 11, line 36, after "compound" insert --of claims 3 or 8--.

Signed and Sealed this

Twelfth Day of September, 1989

*Attest:*

DONALD J. QUIGG

*Attesting Officer*  *Commissioner of Patents and Trademarks*